United States Patent

Southern

(10) Patent No.: US 9,078,593 B2
(45) Date of Patent: Jul. 14, 2015

(54) ULTRASOUND PROBE DEVICE AND METHOD OF OPERATION

(75) Inventor: James Alastair Southern, Reading (GB)

(73) Assignee: FUJITSU LIMITED, Kawasaki (JP)

( * ) Notice: Subject to any disclaimer, the term of this patent is extended or adjusted under 35 U.S.C. 154(b) by 895 days.

(21) Appl. No.: 12/320,837

(22) Filed: Feb. 5, 2009

(65) Prior Publication Data

US 2009/0221917 A1    Sep. 3, 2009

(30) Foreign Application Priority Data

Feb. 5, 2008 (GB) .................. 0802111.5

(51) Int. Cl.
*A61B 8/00* (2006.01)
*A61B 8/08* (2006.01)
*A61B 5/00* (2006.01)

(52) U.S. Cl.
CPC .......... *A61B 8/08* (2013.01); *A61B 5/0048* (2013.01); *A61B 8/485* (2013.01)

(58) Field of Classification Search
CPC ........ A61B 5/0048; A61B 8/485; A61B 8/08; A61B 8/14
See application file for complete search history.

(56) References Cited

U.S. PATENT DOCUMENTS

| | | | |
|---|---|---|---|
| 4,742,829 A | 5/1988 | Law et al. | |
| 5,052,393 A | 10/1991 | Greenstein | |
| 5,070,879 A | 12/1991 | Herres | |
| 5,083,568 A | 1/1992 | Shimazaki et al. | |
| 5,176,142 A | 1/1993 | Mason | |
| 5,320,104 A | 6/1994 | Fearnside et al. | |
| 5,400,790 A | 3/1995 | Pohan et al. | |
| 5,419,329 A | 5/1995 | Smith et al. | |
| 5,485,845 A | 1/1996 | Verdonk et al. | |
| 5,545,942 A | 8/1996 | Jaster et al. | |
| 5,577,507 A | 11/1996 | Snyder et al. | |
| 5,622,177 A | 4/1997 | Breimesser et al. | |
| 5,655,536 A | 8/1997 | Takamizawa | |
| 5,779,639 A | 7/1998 | Yeung | |
| 5,897,503 A | 4/1999 | Lyon et al. | |
| 5,947,905 A | 9/1999 | Hadjicostis et al. | |
| 6,030,346 A | 2/2000 | Buck et al. | |
| 6,036,649 A | 3/2000 | Yuasa | |
| 6,059,728 A | 5/2000 | Ritter | |

(Continued)

FOREIGN PATENT DOCUMENTS

CA    2235947    8/1994
CN    2615666    5/2004

(Continued)

OTHER PUBLICATIONS

Chatillon et al., Ultrasonic non-destructive testing of pieces of complex geometry with a flexible phased array transducer, 2000, Ultrasonics, 38, 131-134.*

(Continued)

*Primary Examiner* — Bo J Peng
(74) *Attorney, Agent, or Firm* — Staas & Halsey LLP

(57) ABSTRACT

An ultrasound probe device including an array of transducers, at least one of which is movable relative to at least one of the other transducers. Each movable transducer may be movable relative to at least one of the other transducers along one axis of movement only, preferably parallel with an initial direction of travel of emitted ultrasound waves relative to the device.

15 Claims, 1 Drawing Sheet

(56) References Cited

U.S. PATENT DOCUMENTS

| | | | |
|---|---|---|---|
| 6,093,150 A | 7/2000 | Chandler et al. | |
| 6,099,474 A | 8/2000 | Solek | |
| 6,100,626 A | 8/2000 | Frey et al. | |
| 6,117,083 A | 9/2000 | Buck et al. | |
| 6,213,948 B1 | 4/2001 | Barthe et al. | |
| 6,241,674 B1 | 6/2001 | Phillips et al. | |
| 6,248,069 B1 | 6/2001 | Liu et al. | |
| 6,423,002 B1 | 7/2002 | Hossack | |
| 6,506,160 B1 | 1/2003 | Van Stralen et al. | |
| 6,508,763 B1 | 1/2003 | Urbano et al. | |
| 6,572,551 B1 | 6/2003 | Smith et al. | |
| 7,249,513 B1 | 7/2007 | Zipparo et al. | |
| 2001/0021809 A1 | 9/2001 | De Jong et al. | |
| 2002/0013529 A1 | 1/2002 | Smith et al. | |
| 2002/0040187 A1* | 4/2002 | Alam et al. | 600/442 |
| 2002/0151790 A1 | 10/2002 | Abend | |
| 2002/0167971 A1 | 11/2002 | Van Stralen et al. | |
| 2003/0018269 A1 | 1/2003 | Angelsen et al. | |
| 2003/0028107 A1 | 2/2003 | Miller et al. | |
| 2003/0055338 A1 | 3/2003 | Steininger et al. | |
| 2004/0064044 A1 | 4/2004 | Brock-Fisher | |
| 2004/0181152 A1 | 9/2004 | Zhang et al. | |
| 2004/0254470 A1 | 12/2004 | Drinkwater et al. | |
| 2004/0267135 A1 | 12/2004 | Takeuchi | |
| 2005/0085731 A1 | 4/2005 | Miller et al. | |
| 2005/0119572 A1 | 6/2005 | Angelsen et al. | |
| 2005/0148873 A1 | 7/2005 | Petersen et al. | |
| 2005/0148877 A1 | 7/2005 | Guo et al. | |
| 2005/0148878 A1 | 7/2005 | Phelps et al. | |
| 2005/0165312 A1 | 7/2005 | Knowles et al. | |
| 2005/0165313 A1 | 7/2005 | Byron et al. | |
| 2005/0203396 A1 | 9/2005 | Angelsen et al. | |
| 2005/0203404 A1 | 9/2005 | Freiburger | |
| 2005/0203416 A1 | 9/2005 | Angelsen et al. | |
| 2005/0277836 A1 | 12/2005 | Proulx et al. | |
| 2005/0277853 A1 | 12/2005 | Mast et al. | |
| 2005/0283079 A1 | 12/2005 | Steen et al. | |
| 2005/0288587 A1 | 12/2005 | Roh et al. | |
| 2006/0030780 A1 | 2/2006 | Gelly et al. | |
| 2006/0052703 A1 | 3/2006 | Kumazawa | |
| 2006/0058656 A1 | 3/2006 | Kristoffersen et al. | |
| 2006/0058667 A1 | 3/2006 | Lemmerhirt et al. | |
| 2006/0184033 A1 | 8/2006 | Cerofolini | |
| 2007/0016026 A1 | 1/2007 | Thomenius et al. | |
| 2007/0016058 A1 | 1/2007 | Kerwin | |
| 2007/0032726 A1 | 2/2007 | Osaka et al. | |
| 2007/0112269 A1 | 5/2007 | Germond-Rouet et al. | |
| 2007/0161905 A1 | 7/2007 | Munrow | |
| 2007/0167808 A1 | 7/2007 | Nozaki | |
| 2007/0167813 A1 | 7/2007 | Lee et al. | |
| 2007/0167824 A1 | 7/2007 | Lee et al. | |
| 2007/0167825 A1 | 7/2007 | Lee et al. | |

FOREIGN PATENT DOCUMENTS

| | | | |
|---|---|---|---|
| CN | 1688255 | 10/2005 | |
| CN | 1688897 | 10/2005 | |
| DE | 19935842 A1 | 2/2000 | |
| DE | 102005051352 A1 | 5/2006 | |
| EP | 2219089 | 11/1989 | |
| EP | 0359546 A2 | 3/1990 | |
| EP | 0388215 A2 | 9/1990 | |
| EP | 0429799 A1 | 6/1991 | |
| EP | 0430450 A2 | 6/1991 | |
| EP | 0476495 A1 | 3/1992 | |
| EP | 0489222 A2 | 6/1992 | |
| EP | 0509297 A1 | 10/1992 | |
| EP | 0697258 A2 | 2/1996 | |
| EP | 1757230 A1 | 2/2007 | |
| EP | 1839580 A1 | 10/2007 | |
| EP | 1854413 A1 | 11/2007 | |
| FR | 2544577 | 10/1984 | |
| GB | 0342874 A2 | 11/1989 | |
| GB | 2408575 | 6/2005 | |
| JP | 2001-258088 | 9/2001 | |
| JP | 2001-309493 | 11/2001 | |
| JP | 2002-330963 | 11/2002 | |
| JP | 2004-89357 | 3/2004 | |
| JP | 2004089357 A * | 3/2004 | A61B 8/00 |
| JP | 2004-358263 | 12/2004 | |
| JP | 2005-152629 | 6/2005 | |
| JP | 2005-199067 | 7/2005 | |
| KR | 2001-0062847 | 7/2001 | |
| MX | 01009116 | 8/2004 | |
| WO | 97/44142 | 11/1997 | |
| WO | 99/24967 | 5/1999 | |
| WO | 03/065070 A1 | 8/2003 | |
| WO | 03/011139 A1 | 12/2003 | |
| WO | 2005/053863 A1 | 6/2005 | |
| WO | 2005/099583 A1 | 10/2005 | |
| WO | 2005/108973 A1 | 11/2005 | |
| WO | 2005/120357 A1 | 12/2005 | |
| WO | 2006/077579 A2 | 7/2006 | |
| WO | 2006/119572 A1 | 11/2006 | |
| WO | 2007/017775 A2 | 2/2007 | |
| WO | 2007/017781 A2 | 2/2007 | |
| WO | 2007/032682 A1 | 3/2007 | |
| WO | 2007/037619 A1 | 4/2007 | |
| WO | 2007/112144 A2 | 10/2007 | |

OTHER PUBLICATIONS

Linear Elasticity, http://www.brown.edu/Departments/Engineering/Courses/EN224/eqnimpl/eqnimpl.html, Feb 1, 2001.*

James Southern, et al., "A Direct Solution Method for the Elasticity Inverse Problem", pp. 1-8, Publication date is Feb. 5, 2009 as indicated by applicant in response filed on Jul. 15, 2014.

James Southern, "Mathematical and Computational Modelling of Ultrasound Elasticity Imaging", Keble College, University of Oxford (Thesis paper submitted for the degree of Doctor of Philosophy, Michaelmas 2006), pp. 1-20 only.

Search Report Under Section 17 (Patent Acts 1977) UK Application No. GB0802111.5; Search Date: Apr. 16, 2008.

James Southern, et al., "Mathematical and Computational Modelling of Ultrasound Elasticity Imaging", Keble College, University of Oxford (Thesis paper Submitted for the degree of Doctor of Philosophy, Michaelmas 2006), pp. 1-262.

* cited by examiner

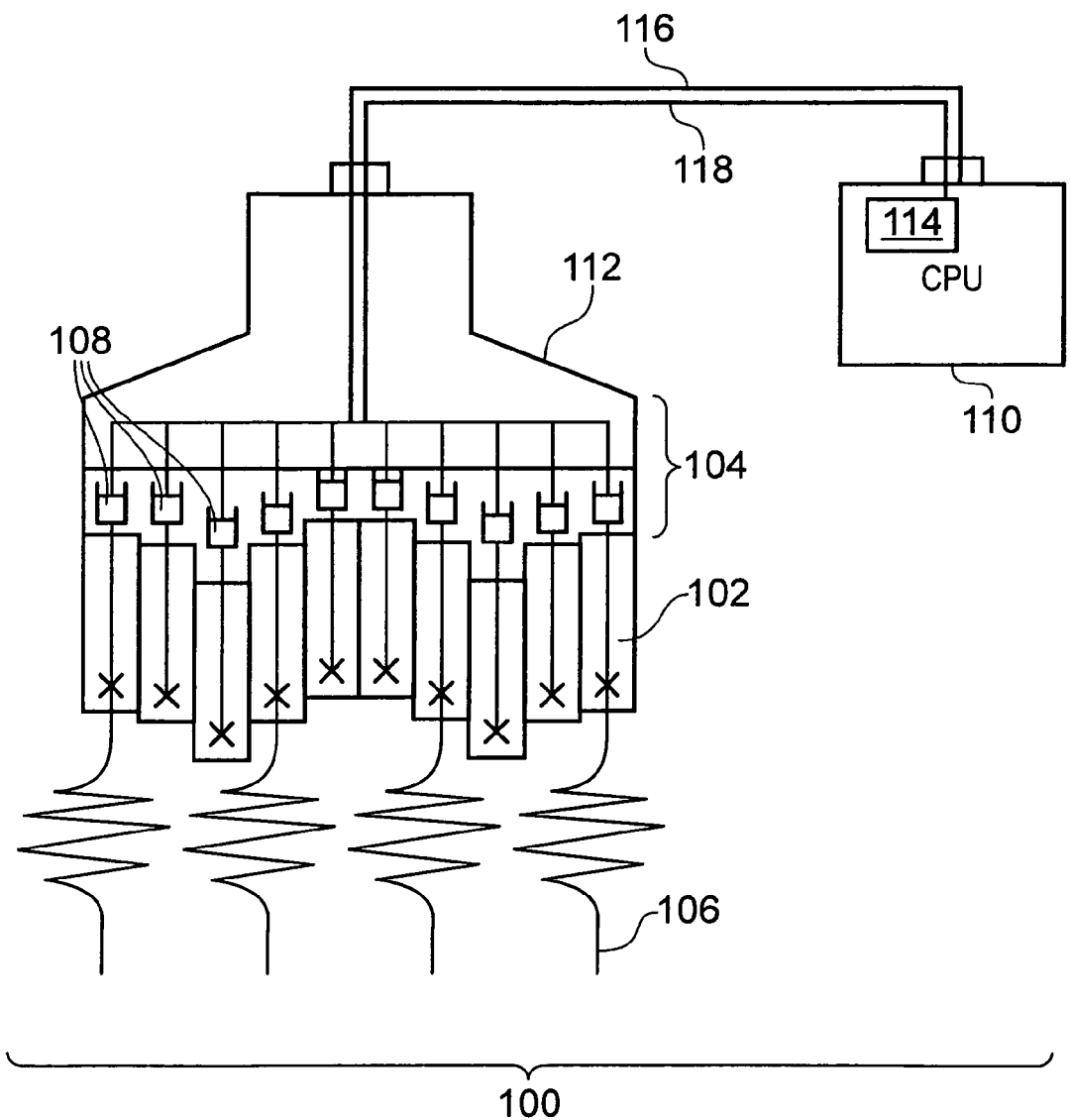

ULTRASOUND PROBE DEVICE AND METHOD OF OPERATION

This application is based upon and claims the benefit of priority of the prior UK Patent Application No. 0802111.5 filed Feb. 5, 2008 in the UK Intellectual Property Office, the entire contents of which are incorporated herein by reference.

The present invention relates to an ultrasound probe device and a method of using the same.

Ultrasound is used in medicine both as a primary imaging tool and in conjunction with other tools. It can be used to produce images of cross sections of regions of interest to clinicians. Ultrasound cannot penetrate bones or pockets of gas so its main function is in imaging soft tissue. Ultrasound is preferred to alternative imaging tools because it does not use ionising radiation, it produces images in real time, and it can be used to give quantitative images of blood flow.

An ultrasound device operating in a conventional "echo" mode works by transmitting a pulse of sound into a region of interest and detecting the echoes received back from within the region. The sound is transmitted from an array of piezoelectric elements, known as the aperture. The received echoes, which are detected by the same piezoelectric elements used for transmission, are used to produce either a 3-dimensional (3-d), or more usually a 2-dimensional (2-d), map of tissue echogenecity.

Medical ultrasound is particularly useful for providing images of tumours in the breast since these are generally surrounded entirely by soft tissue (no bones or lungs between them and the skin) and are not buried too deeply in the body (beyond the effective range of an ultrasound pulse).

The homogeneous wave equation predicts that pressure (sound) waves travelling in a homogeneous medium are non-dispersive and travel in straight lines through the medium. Body tissue, however, is not a homogeneous medium—it contains interfaces between regions with different bulk properties (e.g. cancerous lesions are less compressible than the healthy tissue surrounding them). Furthermore, small fluctuations in the values of density and compressibility about their bulk values are seen within small regions. Both types of inhomogeneity redirect some of the energy of the pressure waves back to the aperture, allowing the formation of ultrasound images. This energy is redirected either via reflection at tissue boundaries, or via scattering from features with dimensions similar to the wavelength of the pressure wave.

An ultrasound image is made up of a combination of sharp lines seen from reflection at tissue boundaries, and the textured speckle generated by scattering elsewhere in the image. Hence the image is inherently noisy (although in medical ultrasound the image and the noise are effectively one and the same), making it difficult to pick out the features of interest as the speckle reduces the contrast between a tumour and the surrounding healthy tissue. One of the methods with the most potential to increase the contrast appears to be elastography (elasticity imaging).

The aim of elastography is to construct an image of the mechanical properties of a region of interest. Fundamentally these properties are a measure of the amount of deformation (strain) an object experiences in response to the application of a known force (stress). Hence, ultrasound elasticity imaging requires at least two ultrasound images of the region of interest. For more accuracy a series of intermediate images must also be used. Each subsequent image must be registered to the first image in order that a series of displacement fields can be estimated. Mathematical models can then be used to estimate the mechanical properties of the tissue and a stiffness field can be generated.

It is desirable to acquire sufficient data to ensure that only one stiffness field is compatible with the observed displacement fields. In general, in order to uniquely solve the equations that determine the tissue stiffness field it is necessary to specify boundary conditions on the stiffness. However, for a general region of tissue we have no a priori way of determining these boundary conditions. The theory tells us that (if the tissue is assumed to be linearly elastic) four linearly independent displacement fields are needed in order to eliminate the need for boundary conditions for a 2-d image (using a linear array probe) and three fields for a 3-d image (using a rectangular array).

Conventionally, generating displacement fields is achieved by pressing the ultrasound probe into the tissue with varying levels of force. For example, United States Patent Application Publication US2007032726 discloses an ultrasound probe including a pressing mechanism for applying a pressing operation perpendicularly to the ultrasound wave transmit/receive surface. However, the resulting displacement fields are not linearly independent (if the tissue is assumed to be linearly elastic then pressing the probe twice as far into the tissue will simply double the displacements everywhere in the region of interest). It is therefore desirable to find a way of generating linearly independent displacement fields in an appropriate manner.

An ultrasound probe device embodying a first aspect of the present invention comprises an array of transducers, wherein at least one of the transducers is movable relative to at least one of the other transducers of the array. This configuration enables the probe to be used to generate linearly independent displacement fields from a sequence of images obtained without removing the probe from a contact surface of a region of interest.

Desirably, in an ultrasound probe device according to an embodiment of the present invention, the, or each, movable transducer is movable relative to at least one of the other transducers along one axis of movement only. Preferably, in the case where the movable transducers are a plurality of transducers, the axes of movement are mutually parallel.

In a device embodying the present invention, it is desirable for each axis of movement to be parallel with an initial direction of travel of emitted ultrasound waves relative to the device.

Another embodiment of the present invention further comprises a driver for applying a driving force to at least one of the transducers thereby to move those transducers along their respective axes of movement.

The driver according to an embodiment of the present invention comprises a plurality of actuators associated with respective ones of the plurality of transducers, each actuator being operable to apply a driving force to an associated one of the transducers thereby to move its associated transducer along its respective axis of movement.

In another embodiment of the present invention the, or each, movable transducer is configurable to change a contact profile of the device by changing the position of the end of the, or each, movable transducer operable to emit ultrasound waves relative to the end operable to emit ultrasound waves of at least one other transducer.

A device according to an embodiment of the present invention further comprises a controller for controlling the driver as to the extent to which the, or each, movable transducer should be moved, and when the movement should occur.

In one embodiment of the present invention the array of transducers is a linear array having only one row of transducers. In another embodiment, the array of transducers is arranged as a 2-dimensional array having more than one row of transducers.

In a device embodying the present invention the controller is operable to instruct the transducers to emit ultrasound pulses in a manner that they either converge or diverge as they move away from the transducers.

An embodiment according to a second aspect of the present invention is a method of using an ultrasound probe device to carry out an elastography imaging process comprising at least two image taking steps of taking an ultrasound image using an ultrasound probe device comprising an array of transducers, wherein at least one of the transducers is movable relative to at least one of the other transducers of the said array, following a first such image taking step, each subsequent image taking step is preceded by a step of changing the configuration of the transducers by enacting movement of at least one movable transducer relative to at least one other transducer of the array, and maintaining contact between the ultrasound probe device and a region of interest throughout the entire process.

In another embodiment of a second aspect of the present invention, the step of changing the configuration of the transducers is controlled by communication between the transducers and a controller via a control communicator 118. This control communicator 118 could take the form of, for example, a wire or set of wires running from the CPU 110 and into the outer casing 112 via an entry at the opposite end of the device to the contact profile, and then connecting to the components as required within the outer casing 112.

A further embodiment of a second aspect of the present invention comprises generating a linearly independent displacement field from each image taking step and then performing a calculation step to generate a stiffness field compatible with the obtained linearly independent displacement fields.

Reference will now be made, by way of example, to the accompanying drawing, in which:

FIG. 1 is a diagram showing an ultrasound probe device embodying the present invention.

As shown in FIG. 1, an ultrasound probe device 100 embodying the present invention comprises an array of piezoelectric transducers 102. In the present embodiment, each of the transducers is movable along an axis parallel to the initial direction of travel of emitted sound waves relative to the device, but a device embodying the present invention may comprise an array of transducers in which fewer of the transducers are movable, for example an array in which only one is movable. Preferably, the transducers 102 are several centimeters or more in length and approximately a millimeter in diameter, and are positioned parallel to one another in the array so that, when viewed end-on, the centre to centre separation of neighbouring transducers 102 is of the order of a millimeter.

The array may be a linear array comprising only one row of perhaps up to a hundred transducers 102, or the array may take a different form, for example a rectangular or approximately circular array with each row comprising tens or hundreds of transducers 102.

A device embodying the present invention also comprises a driver 104 connected and arranged for bringing about movement of the transducers. In the present embodiment, the driver 104 is arranged at one end of the array of transducers 102. The driver 104 may be an array of actuators 108, each associated with one or more transducers 102. There are numerous possibilities as to the exact nature of these actuators 108, but they could be for example, electromechanical, or they could be pneumatic or hydraulic.

In a device embodying the present invention the entire assembly of transducers 102 and the driver 104 are at least partially housed in an outer casing 112. The distal (when viewed with respect to the driver 104) ends of the transducers 102 may be exposed, or the distal end of the entire array may be covered by a flexible sheath. The external shape formed by the combination of the distal ends of the array of transducers 102 in combination is defined herein as a contact profile of the device, i.e. the profile of the device which contacts the subject undergoing ultrasound imaging. The movable nature of the transducers means that there will be discontinuities in the contact profile of the device. It is desirable to keep these discontinuities as small as possible, hence a large number of transducers is preferable.

A device embodying the present invention further comprises a controller 114. The controller 114 may be a CPU 110, or a component of a CPU 110, and may or may not be housed within the outer casing 112. Means of communication 118 between the controller 114 and the driver 104 are provided. In the case where the controller 114 is not housed within the outer casing 112, the means of communication could take the form of, for example, a wire or set of wires running from the controller 114 and into the outer casing 112 via an entry at the opposite end of the device to the contact profile, and then connecting to the components as required within the outer casing 112. Each actuator 108 and each transducer 102 has some means of communication with the controller 114.

A device embodying the present invention comprises a CPU 110. Means of communication between the CPU 110 and the transducers 102 are provided via a CPU communicator 116. This CPU communicator 116 could take the form of, for example, a wire or set of wires running from the CPU 110 and into the outer casing 112 via an entry at the opposite end of the device to the contact profile, and then connecting to the components as required within the outer casing 112. Each transducer 102 has means of communication with the CPU 110.

Each transducer 102 is operable to receive an electrical signal from the controller 114, and to convert it into a sound wave to be emitted from the distal end of the transducer 102 into a region of interest. Medical ultrasound devices usually emit sound waves with a frequency between 2 and 18 MHz. In a device for imaging a breast, a typical ultrasound pulse might have a frequency in the range 7.5-12 MHz. The controller 114 can slightly stagger the times at which each of the transducers 102 emits its sound waves in order to focus the overall wave pulse (this is known as beam forming). An alternative method for focussing the direction and depth of the beam is to use a phased array technique, whereby the controller 114 is able to manipulate the relative phases of the emitted waves.

The emitted sound waves can then be reflected or scattered by tissue boundaries or small features in the region of interest. This reflected and scattered sound is known as the echo. Any portion of the echo incident upon a piezoelectric transducer 102 of the probe device is then converted back into an electrical signal and sent via the communicator to the CPU 110. The CPU 110 can then generate an ultrasound image based on the intensity (calculated for example, from the amplitude of the electrical signal) and timing of the electrical signal received from each transducer.

One embodiment of the present invention is operable to emit ultrasound pulses from each, or groups of, transducer(s) in sequence, and an image is built up based on the timings of echoes received from the pulses. This is especially useful in an embodiment whereby the emitted ultrasound waves are either deflected before entry into the region of interest, or are emitted in a manner such that they converge or diverge as they travel away from the probe. It may be desirable to emit ultrasound waves in a manner such that they converge to either focus the waves on a small region of interest or in order to increase the resolution of the image. Conversely, an image of a larger region of interest with a lower resolution can be obtained by emitting waves in a manner such that they diverge from the probe device.

In an embodiment of the present invention, the driver 104 is operable to move one or more of the transducers 102 relative to at least one or more other transducers 102. Any movement of a transducer 102 relative to another performed by the driver 104 is along the axis of movement of the, or each, respective transducer. This axis of movement is parallel to the direction in which an emitted ultrasound wave would travel relative to the device. Moving the transducers 102 in this way is carried out by the driver 104 in accordance with instructions received from the controller 114. When they are not moving, the transducers 102 are fixed in position. This enables the controller 114 to engender a change in the contact profile of the device.

In an embodiment of the present invention the driver 104 comprises a plurality of actuators 108. These actuators 108 are each associated with one, or a group of, transducers 102. When an appropriate instruction is received from the controller 114, the actuators 108 are operable to apply a driving force to their associated transducer(s) 102. When the transducers 102 are not being moved by their respective actuator, their positions relative to one another are fixed. In this way, the controller 114 is operable to dictate the extent to which each actuator 108 should move its associated transducer or transducers 102 thereby to engender a change in the contact profile of the device.

The number of possible contact profile shapes is limited by the extent to which the or each movable transducer can move along its axis of movement, and the number of points within this range of movement at which its position can be fixed. The number of different configurations of contact profile N is given by $N=p^t$, where t is the number of movable transducers 102 and p the number of potential fixed positions within the range of movement of the, or each, movable transducer. Although the number of potential contact profiles is large (for example, 100 movable transducers 102 each with a choice of 10 fixed positions gives $10^{100}$ possible contact profiles), it is preferable that gradients on the profile whilst obtaining an image are shallow.

In one embodiment of the present invention, the end of the outer casing 112 distal from the contact profile forms what is effectively a handle. Depending on the dimensions of the device, the outer casing 112 may taper from a wider cross section at the contact profile end into a thinner cross section at the distal end. The handle should be formed such that a human operator may exert a firm grip on the device. In an alternative embodiment, the handle may be suitable to be held firmly by a mechanical brace or fixed in position by some other means.

Embodiments of the present invention are operable to perform elastography (elasticity imaging) of human tissue. When used in this way, a water based gel is applied to the area skin on which the contact profile of the device is to be placed. This reduces the portion of the ultrasound pulse reflected at the device/skin boundary, or the device/air/skin boundaries in the case where the device is not in immediate contact with the skin. In this way the amount of the ultrasound pulse entering the region of interest is optimised.

Throughout the entire elastography imaging process, the device should be held so that the position or angle of the contact profile relative to the region of interest is maintained. The device should be held firmly so that an approximately constant pressure is applied to the region of interest. At the beginning of the process, an initial ultrasound image of the region of interest is obtained. The transducers 102 are then moved and fixed in their new position according to instructions issued to the driver 104 from the controller 114, so that the contact profile of the device is changed. The contact profiles used in an entire imaging process should be different from one another. The region of interest is then re-imaged. This cycle of changing contact profile and imaging can continue a number of times until the process is deemed to be complete. This number may be pre-determined, or may be decided during the imaging process by the operator according to the quality of images obtained.

For each ultrasound image that can be referenced back to either the initial image, or a nominal reference image (form the same sequence), the CPU 110 is operable to generate displacement fields. Displacement estimation is an active field of research, though current methods that may be used by an embodiment of the present invention include differential methods, frequency based methods, and block-matching displacement estimation. Because of the different contact profile used for each image, the displacement fields so obtained are linearly independent from one another. Based on these displacement fields, the CPU 110 is operable to generate a stiffness field (image).

Embodiments of the present invention use parameter recovery methods to obtain a stiffness field from a sequence of displacement fields. As mentioned previously, theoretically (if the tissue is assumed to be linearly elastic) four linearly independent displacement fields are needed in order to eliminate the need for boundary conditions for a 2-d image (using a linear array probe) and three fields for a 3-d image (using a rectangular or approximately circular array). Several parameter recovery methods are available. In an embodiment of the present invention, a method using linear elasticity models for the soft tissue in the region of interest and finite element methods to determine tissue properties from given displacement fields is preferred.

Oil and gas exploration represent another potential application of a device embodying the present invention. The physical dimensions of such a device would probably be significantly larger than those of a device intended for medical use. The use of ultrasound in oil and gas exploration is an example of a surface seismic method. These are methods in which ultrasound waves are transmitted into the ground above a region of interest, and the resultant echoes can be used to construct an image of the sub-surface geology.

The invention claimed is:

1. An ultrasound probe device having a probe surface, configured for contact with a region of interest, which surface defines a contact profile of the device, the device comprising:
    an array of transducers, wherein at least one of the transducers is movable relative to at least one of the other transducers of the said array, each movable transducer being configurable to change the contact profile of the device by changing the position of the end of the or each movable transducer operable to emit ultrasound waves relative to the end of at least one other transducer, the array of transducers being configured to carry out an elastography imaging process in which at least two ultrasound images are obtained whilst the device is in contact with a region of interest, wherein the contact profile is an external shape formed by a combination of distal ends of the array of transducers;

a processor via a control communication configured to bring about change in a configuration of the transducers, after a first such image is obtained, by enacting movement of at least one movable transducer relative to at least one other transducer of the array before obtaining each subsequent image, thereby to engender a change in the contact profile of the device with the region of interest whilst contact between the ultrasound probe device and the region of interest is maintained and so displace part of the region of interest between images;

and the processor further configured to generate a linearly independent displacement field from each image without removing the ultrasound probe device from contact with the region of interest as relative position of the transducer is changed, where the relative position of the transducer is changed by using different levels of driving forces to the transducers and to calculate a stiffness field compatible with the obtained linearly independent displacement fields.

2. The ultrasound probe device according to claim 1, wherein each said movable transducer is movable relative to said at least one of the other transducers along one axis of movement only.

3. The ultrasound probe device according to claim 2, wherein said movable transducers comprise a plurality of transducers having respective axes of movement which are mutually parallel.

4. The ultrasound probe device according to claim 3, wherein the, or each, axis of movement is parallel with an initial direction of travel of emitted ultrasound waves relative to the device.

5. The ultrasound probe device according to claim 3, further comprising: a driver configured to apply one of the driving forces to at least one of the transducers thereby to move said at least one of the transducers along the respective axis of movement.

6. The ultrasound probe device according to claim 2, wherein each axis of movement is parallel with an initial direction of travel of emitted ultrasound waves relative to the device.

7. The ultrasound probe device according to claim 6, further comprising: a driver configured to apply one of the driving forces to at least one of the transducers thereby to move said at least one of the transducers along the respective axis of movement.

8. The ultrasound probe device according to claim 2, further comprising:

a driver configured to apply one of the driving forces to at least one of the transducers thereby to move said at least one of the transducers along the respective said axis of movement.

9. The ultrasound probe device according to claim 8, wherein the driver comprises a plurality of actuators associated with respective ones of the plurality of transducers, each actuator being operable to apply one of the driving forces to an associated one of the transducers thereby to move said associated transducer along its respective axis of movement.

10. The ultrasound probe device according to claim 8, wherein the processor via the control communication configured to control the driver as to the extent to which each movable transducer should be moved, and when the movement should occur.

11. The ultrasound probe device according to claim 10, wherein the processor via the control communication configured to instruct the transducers to emit ultrasound pulses in such a manner that they either converge or diverge as they move away from the transducers.

12. The ultrasound probe device according to claim 1, wherein the array of transducers is a linear array having only one row of transducers.

13. The ultrasound probe device according to claim 1, wherein the array of transducers is arranged as a 2-dimensional array having more than one row of transducers.

14. An apparatus to carry out an elastography imaging process the apparatus having a probe surface, configured for contact with a region of interest, which surface defines a contact profile of the apparatus, the apparatus comprising:

an ultrasonic probe device comprising an array of transducers where at least one of the transducers is movable relative to at least one of the other transducers of said array each movable transducer being configurable to change the contact profile of the ultrasonic probe device, wherein the contact profile is an external shape formed by a combination of distal ends of the array of transducers;

a processor configured to have at least two image taking steps of taking an ultrasound image via the ultrasonic probe device, and following a first such image taking step, each subsequent image taking step is preceded by a step of changing a configuration of the transducers by enacting movement of at least one movable transducer relative to at least one other transducer of the array and maintaining contact between the ultrasonic probe device and a region of interest throughout the entire elastography imaging process;

and the processor further configured to generate a linearly independent displacement field from each image taking step without removing the ultrasonic probe device from contact with the region of interest as relative position of the transducer is changed and to calculate a stiffness field compatible with the obtained linearly independent displacement field.

15. An apparatus according to claim 14, wherein the processor changes the configuration of the transducers via a control communication between the transducers and the processor.

* * * * *